US010792066B2

(12) United States Patent
Parsell et al.

(10) Patent No.: US 10,792,066 B2
(45) Date of Patent: Oct. 6, 2020

(54) MEDICAL IRRIGATION DEVICE AND METHOD

(71) Applicant: Bone Foam, LLC, Plymouth, MN (US)

(72) Inventors: Doug Parsell, Ridgeland, MS (US); Chad Robran, Plymouth, MN (US)

(73) Assignee: BONE FOAM, INC., Corcoran, MN (US)

( * ) Notice: Subject to any disclaimer, the term of this patent is extended or adjusted under 35 U.S.C. 154(b) by 161 days.

(21) Appl. No.: 13/766,063

(22) Filed: Feb. 13, 2013

(65) Prior Publication Data

US 2013/0211425 A1  Aug. 15, 2013

Related U.S. Application Data

(60) Provisional application No. 61/633,464, filed on Feb. 13, 2012.

(51) Int. Cl.
| | |
|---|---|
| *A61G 15/00* | (2006.01) |
| *A61B 17/3203* | (2006.01) |
| *A61B 46/27* | (2016.01) |
| *A61M 3/02* | (2006.01) |
| *A61M 1/00* | (2006.01) |
| *A61B 46/20* | (2016.01) |

(52) U.S. Cl.
CPC .......... *A61B 17/3203* (2013.01); *A61B 46/27* (2016.02); *A61M 1/0088* (2013.01); *A61M 3/0287* (2013.01); *A61B 2046/201* (2016.02)

(58) Field of Classification Search
CPC .... A61M 1/00; A61M 3/0266; A61M 3/0287; A61B 19/12; A61B 19/08; A61B 2019/106; A61B 2019/385; A61B 2019/086; A61B 2019/084; A61B 19/38

USPC ........ 604/290, 289; 128/845, 849, 856, 853, 128/854, 855

See application file for complete search history.

(56) References Cited

U.S. PATENT DOCUMENTS

| | | | |
|---|---|---|---|
| 3,762,404 | A | 10/1973 | Sakita |
| 3,873,081 | A | 3/1975 | Smith |
| 4,136,858 | A | 1/1979 | Peterson |
| 4,194,601 | A | 3/1980 | Yellin |
| 4,218,792 | A | 8/1980 | Kogan |

(Continued)

OTHER PUBLICATIONS

ISR and Written Opinion for PCT Application No. PCT/US2014/014913 dated Apr. 25, 2014.

*Primary Examiner* — Victoria J Hicks
(74) *Attorney, Agent, or Firm* — Workman Nydegger

(57) ABSTRACT

An apparatus for supporting an extremity during tissue debridement and capturing fluid and tissue resulting from tissue debridement includes an extremity-supporting base and barrier shroud. The apparatus can be used in tissue debridement procedures to contain and control drainage of fluid and tissue. The apparatus supports and encloses a patient extremity, such as an arm or a leg. The base has a length, proximal end (i.e., nearest the patient's body), and distal end (i.e., farthest from the patient's body). The shroud has a top portion, bottom portion, and shroud drainage opening. A method includes debriding tissue from a patient extremity while supported by the base and at least partially enclosed within the barrier shroud, which acts as a shield for fluid and tissue emanating from the extremity. Fluid and tissue exits the shroud through a shroud drainage opening.

20 Claims, 7 Drawing Sheets

(56) References Cited

U.S. PATENT DOCUMENTS

| | | | |
|---|---|---|---|
| 4,481,943 A | 11/1984 | Michalson | |
| 4,620,698 A | 11/1986 | Reed | |
| 4,681,309 A | 7/1987 | Lechner | |
| 4,742,981 A | 5/1988 | Converse | |
| 4,745,647 A | 5/1988 | Goodwin | |
| 4,836,523 A | 6/1989 | Englander | |
| 4,863,788 A | 9/1989 | Bellairs | |
| 4,974,604 A * | 12/1990 | Morris | A61B 46/00 128/853 |
| 5,014,375 A | 5/1991 | Coonrad | |
| 5,016,268 A | 5/1991 | Lotman | |
| 5,125,123 A | 6/1992 | Engle | |
| 5,178,162 A | 1/1993 | Bose | |
| 5,289,828 A | 3/1994 | Toth | |
| 5,312,385 A | 5/1994 | Greco | |
| 5,316,541 A | 5/1994 | Fischer | |
| 5,369,825 A | 12/1994 | Reesby | |
| 5,381,562 A * | 1/1995 | Holloway | A45D 19/06 4/516 |
| 5,437,602 A | 8/1995 | Polyakov et al. | |
| 5,439,008 A * | 8/1995 | Bowman | A47D 13/08 128/845 |
| 5,462,551 A | 10/1995 | Bailey | |
| 5,584,303 A * | 12/1996 | Walle | A61F 5/01 128/882 |
| 5,609,163 A | 3/1997 | Beard | |
| 5,645,079 A | 7/1997 | Zahiri | |
| 5,754,997 A | 5/1998 | Lüssi | |
| 5,775,334 A | 7/1998 | Lamb | |
| 5,809,597 A | 9/1998 | Shaw | |
| 5,819,743 A | 10/1998 | McMillan | |
| 5,836,309 A | 11/1998 | Webb | |
| 5,906,205 A | 5/1999 | Hiebert | |
| 6,032,669 A | 3/2000 | Klein | |
| 6,402,724 B1 | 6/2002 | Smith et al. | |
| 6,405,389 B1 * | 6/2002 | Harty | A47K 3/062 4/621 |
| 6,553,995 B1 | 4/2003 | Cole et al. | |
| 7,678,092 B2 * | 3/2010 | Matloub | A61F 13/00038 128/855 |
| 8,726,907 B2 * | 5/2014 | Strauch et al. | 128/849 |
| 2004/0225265 A1 | 11/2004 | Tapadiya | |
| 2011/0297164 A1 * | 12/2011 | Strauch | A61B 19/088 128/849 |

* cited by examiner

MEDICAL IRRIGATION DEVICE AND METHOD

CROSS REFERENCE TO RELATED APPLICATION

The Application claims the benefit of earlier filed U.S. Provisional Application No. 61/633,464, filed Feb. 13, 2012, the disclosure of which is incorporated herein in its entirety.

BACKGROUND OF THE INVENTION

1. The Field of the Invention

The present invention relates to devices and methods for use in removing biological debris from patient extremities. More specifically, the present invention relates to medical irrigation devices and methods for containing the fluid and solid biological debris ejected as a result of debridement using high-pressure jetted fluid.

2. Background and Relevant Art

Within the medical arts, it is common practice to remove infected and/or necrotic tissues to allow for increased healing rates and to decrease infection risk. The clinical procedure for the above-mentioned action is termed wound debridement. A common component of the debridement process is copious fluid irrigation of the targeted tissue areas. The fluids used are typically sterile saline but fluid with additional antimicrobial agents may also be utilized.

In general, known techniques for tissue debridement include surgical, chemical, mechanical, and autolytic. Surgical debridement techniques include conventional surgical techniques, involving the use of sharp medical instruments, and hydrosurgical techniques, involving the use of a high-pressure stream or spray of jetted fluid.

In hydrosurgical debridement, infected and/or necrotic tissue (i.e., tissue that is dead, burned, diseased, infected, etc.), is ablated using a stream or spray of water, saline, or other fluid directed under very high pressure at the tissue to be removed. Because large amounts of fluid are required, and because the high pressure of the fluid against the targeted necrotic tissue can result in uncontrolled emission of fluid as well as the ablated pieces of infected and/or necrotic tissue, hydrosurgical debridement can be unsanitary and messy.

Uncontrolled tissue and fluid emission associated with hydrosurgical debridement can create problems for medical staff, such as contamination of equipment, clothing, face shields or eye protection. In addition, hydrosurgical debridement procedures can require the complete turnover and re-sterilization of some or all of equipment in the operating room, as well as a thorough disinfection and sterilization of every surface in the operating room. Turnover, sterilization and disinfection procedures are labor-intensive, time-consuming, and expensive.

As such, there exists a need for extremity supporting structures that facilitate the effective and convenient deployment of the irrigation and debridement process.

BRIEF SUMMARY

Disclosed herein are embodiments of apparatus for supporting an extremity during tissue debridement and capturing fluid and tissue resulting from tissue debridement and methods of debriding tissue of an extremity and capturing fluid and tissue resulting from tissue debridement. The apparatus and methods can provide improved sanitary conditions for a patient and medical personnel involved in a tissue debridement procedure, as well as a cleaner environment in the operating room.

According to one embodiment, an apparatus for supporting an extremity during tissue debridement and capturing fluid and tissue includes an extremity-supporting base configured to support an extremity of a patient during tissue debridement. The base can have a proximal end positioned nearest a patient's body during use and a distal end opposite the proximal end. A barrier shroud can be positionable so as to at least partially enclose an extremity placed on the extremity-supporting base. A drainage passageway can be provided that is in fluid communication with the extremity-supporting base and barrier shroud, which provides controlled drainage of fluid and tissue from the extremity-supporting base and barrier shroud during tissue debridement.

The extremity-supporting base may include a trough, such as a concave trough, for cradling an extremity. The trough may have a trough bottom and a side wall on either side of the trough bottom. The extremity-supporting base may be downwardly angled toward the drainage passageway to facilitate movement of fluid and tissue toward the drainage passageway during tissue debridement. According to one embodiment, the drainage passageway is positioned at or near the distal end of the base to facilitate movement of fluid and tissue away from the patient's body during tissue debridement. The drainage passageway can be provided by a hole through the base and/or barrier shroud. A drainage tube may be attached to the drainage passageway to facilitate drainage of fluid and tissue into a receiving vessel. Drainage may be gravitational or aspiration assisted.

According to one embodiment, the barrier shroud comprises a flexible sheet material, such as a water-proof polymer. One or more braces that cooperate with the flexible barrier shroud may advantageously maintain the barrier shroud in a desired elevated configuration above the extremity-supporting base and relative to an extremity during tissue debridement (e.g., to provide space between the shroud and extremity). The barrier shroud may include one or more fasteners that permit selective opening and closing of the barrier shroud relative to an extremity placed on the extremity-supporting base. The barrier shroud may include an opening in an upper region that permits access to the extremity by a debridement instrument, such as a high pressure irrigation device.

According to one embodiment, the extremity-supporting base may be formed from an open-cell foam material (e.g., flexible polyurethane foam). A flexible, fluid-impermeable coating may be positioned over at least a portion of the open-cell foam material to provide additional sterility and ease of cleaning.

According to another embodiment, a method of debriding tissue of an extremity and capturing fluid and tissue resulting from tissue debridement includes: (1) placing an extremity of a patient on an extremity-supporting base; (2) at least partially enclosing said extremity with a barrier shroud; and (3) debriding a portion of said extremity using a high-pressure fluid, (4) the base and barrier shroud substantially containing fluid and tissue resulting from tissue debridement and controlling drainage of said fluid and tissue. The method may include gravitational and/or aspiration assisted drainage of fluid and tissue through a drainage hose in fluid communication with the barrier shroud and base.

This Brief Summary is provided to introduce in a simplified form a selection of concepts that are further described below in the Detailed Description. This Brief Summary is not intended to identify key or essential features of the claimed subject matter, nor is it intended to be used as an aid in determining the scope of the claimed subject matter. Additional features and advantages of the invention will be set forth in the description which follows, and in part will be evident to persons of ordinary skill in the art from the description and appended claims, or may be learned by such persons through the practice of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not necessarily drawn to scale, and that elements of similar structure or function are generally represented by like reference numerals for illustrative purposes throughout the figures. These drawings depict only certain embodiments of the invention and are not therefore to be considered to be limiting of its scope.

DETAILED DESCRIPTION

Figure 1:
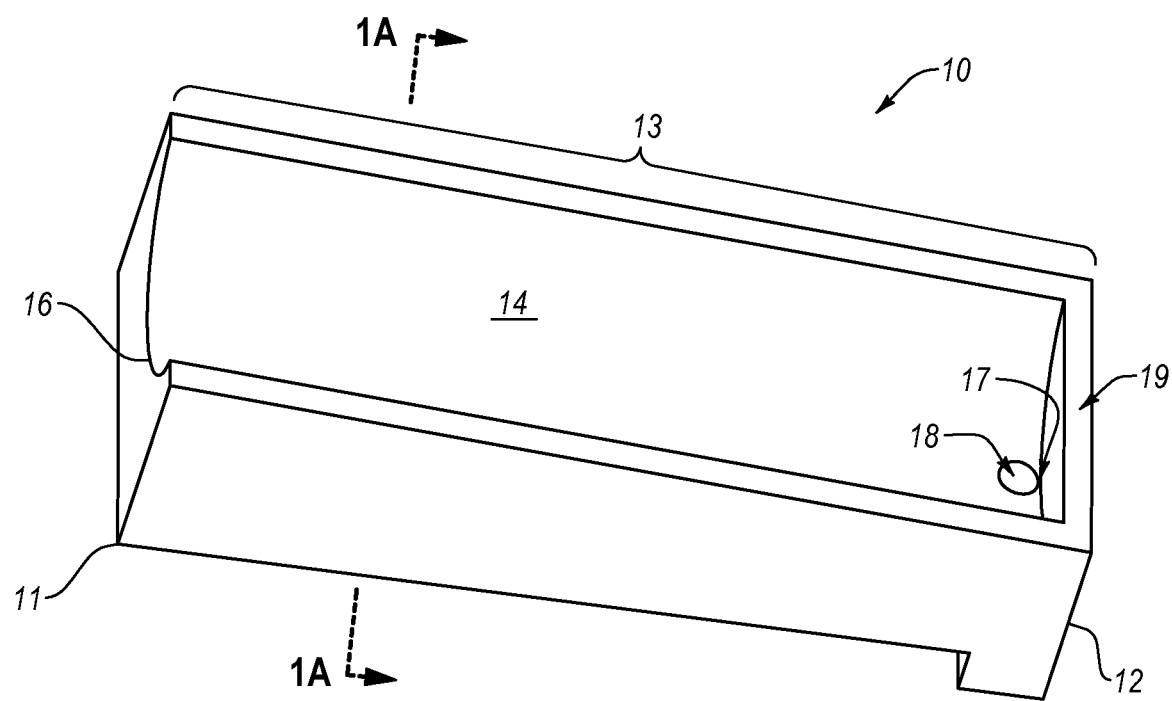
FIG. 1 is an example embodiment of an extremity-supporting base having a downward sloping concave trough with a dam and drainage opening at a distal end.

The following are example embodiments of apparatus for supporting an extremity during tissue debridement and capturing fluid and tissue resulting from tissue debridement and methods of debriding tissue of an extremity and capturing fluid and tissue resulting from tissue debridement. According to one embodiment, an extremity supporting medical irrigation ramp (or apparatus for supporting an extremity during tissue debridement and capturing fluid and tissue resulting from tissue debridement) is composed of two elements: an extremity-supporting, fluid-channeling element (or extremity-supporting base) and a sterile, barrier element (or barrier shroud). In one embodiment, the extremity-supporting base may be constructed from open cell foam material at least partially covered with a fluid impermeable, flexible exterior coating. The exterior coating is may comprise a polymeric, non-latex composition.

The extremity-supporting base may include a concave surface that supports the patient's extremity (e.g., arm or leg). The concavity of the extremity-supporting element can function to channel fluids applied during the debridement procedure, and also tissue removed during debridement, toward a distal end of the device. The extremity-supporting base may further include a downward slope, which slopes downward toward a distal end of the extremity-supporting base. In one embodiment, a dam feature at a distal end of the apparatus allows for pooling of applied fluids and removed tissues. A drainage hole at or near the distal end allows for the continuous removal/evacuation of fluids and tissue. The dam might form part of the extremity-supporting base and/or it may be part of the barrier shroud.

For each individual debridement case (i.e., each new patient extremity), a new sterile, barrier element or shroud may be used by placing it between the patient's extremity and the extremity-supporting base. In this way, the extremity-supporting base can be kept sterile and re-used if desirable, while the barrier shroud is a single-use, disposable feature. Alternatively, the base may itself be disposable. The barrier shroud can be a smooth plastic sheet that easily conforms to the concave shape of the extremity-supporting base and is advantageously of adequate size to cover all potential patient extremity-contacting surfaces of the extremity-supporting base.

According to one embodiment, the barrier element may include a drainage hole and an integrated, semi-rigid drainage tube that is of a diameter to slide into a drainage hole at the distal extent of the extremity-supporting base (when included). The drainage tube can be of sufficient length to extend significantly beyond the bottom surface of the extremity-supporting base, when fully engaged. Alternatively, a drainage tube can be attached to the drainage hole of the barrier element when positioned beyond a distal end of the extremity-supporting element. The drainage tube allows for fluids applied during the debridement procedure to exit the device via gravity-assisted, fluid movement into a receiving vessel or, alternatively, via suction assisted evacuation of fluids.

To further capture fluid droplets that may possess an upwards trajectory during the debridement procedure, the sterile covering element or shroud may comprise a "green house" structure (e.g., by means of hoops or braces that hold the barrier shroud in a desired configuration during use). This feature can attach at the lateral edge of the device and arch over the extremity. The "green house" structure can be made from clear plastic to allow for adequate visualization of the debridement field. Right and left side slits may run along the length of the "green house" structure, so as to allow for insertion of a tip of an irrigation device through the plastic barrier and direct access to the debridement site.

The top portion of the barrier shroud may include an opening formed therein to allow a hydrosurgical debridement device to access the debridement site of the extremity. The top portion and bottom portion may be joined together around the edges in either a permanent manner or in a manner designed to allow the shroud to be opened and closed (e.g., like a sleeping bag). The top portion and bottom portion of the shroud may include fasteners such as snaps, Velcro® (hook and loop), zippers, hooks, clasps, or other fastening elements known in the art which can allow the shroud to be selectively opened and closed.

Referring now to FIG. 1, an embodiment of an extremity-supporting base 10 is shown. Base 10 has a proximal end 11 and a distal end 12 defining a length 13 between proximal end 11 and distal end 12. Proximal end 11 is typically positioned nearest to the patient's body (e.g., torso in the case of a leg or shoulder in the case of an arm). Distal end 12 is typically the end farthest away from the patient's body.

Figure 1A:
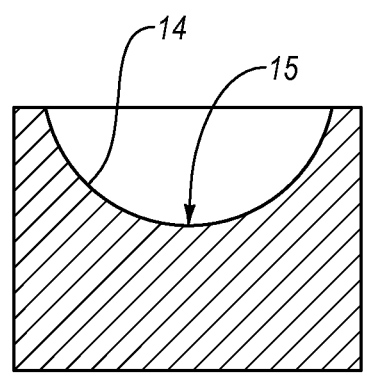
FIG. 1A is a transverse cross-sectional view of FIG. 1.

Base 10 is configured for use as a support for a patient extremity, such as an arm or a leg, which can be further enclosed within a shroud, discussed below, during the process of hydrosurgical wound debridement. According to one embodiment, base 10 can have a concave support surface to help cradle and hold a patient extremity in a desired orientation, and which can direct fluid and tissue debris associated with hydrosurgical debridement toward the lowest point of a downwardly sloping support surface. Base 10 may therefore be constructed such that a trough 14 having a concave shape extends along part or all of the length 13 of base 10. Trough 14 as illustrated includes a trough bottom 15 that also runs along part or all of the length 13 of base 10. Trough 14 and trough bottom 15 are more particular illustrated in FIG. 1A, which is a cross-sectional view of base 10 as seen from proximal end 11.

To control runoff of fluid and tissue debris associated with a debridement procedure, trough 14 can be sloped downward along the base length 13 from a high point 16 at proximal end 11 to low point 17 at distal end 12. In the illustrated embodiment, positioned at or near the low point 17 is a base drainage opening or passageway 18. A base dam 19 is positioned at distal end 12 in close proximity to base drainage opening 18 such that excess fluid and tissue debris associated with debridement can build-up in the area adjacent to base drainage opening 18, which facilitates controlled drainage of such fluid and tissue debris through passageway or hole 18. Drainage can be by gravity alone or assisted by applied vacuum suction.

In an alternative embodiment (not shown), the trough bottom may include more than one high point and either side of a low point. The multiple high points and trough bottom low point may be arranged such that a trough bottom low point is located at or near the center of the base to promote drainage through a passageway at this location. Alternatively, the trough bottom may include a high point in the center and low points at the proximal and distal ends.

Base 10 may be made of open-cell foam and may have a coating thereof that is fluid-impermeable and flexible. The coating on base 10 may be formed of a polymeric, non-latex composition.

Figure 2:
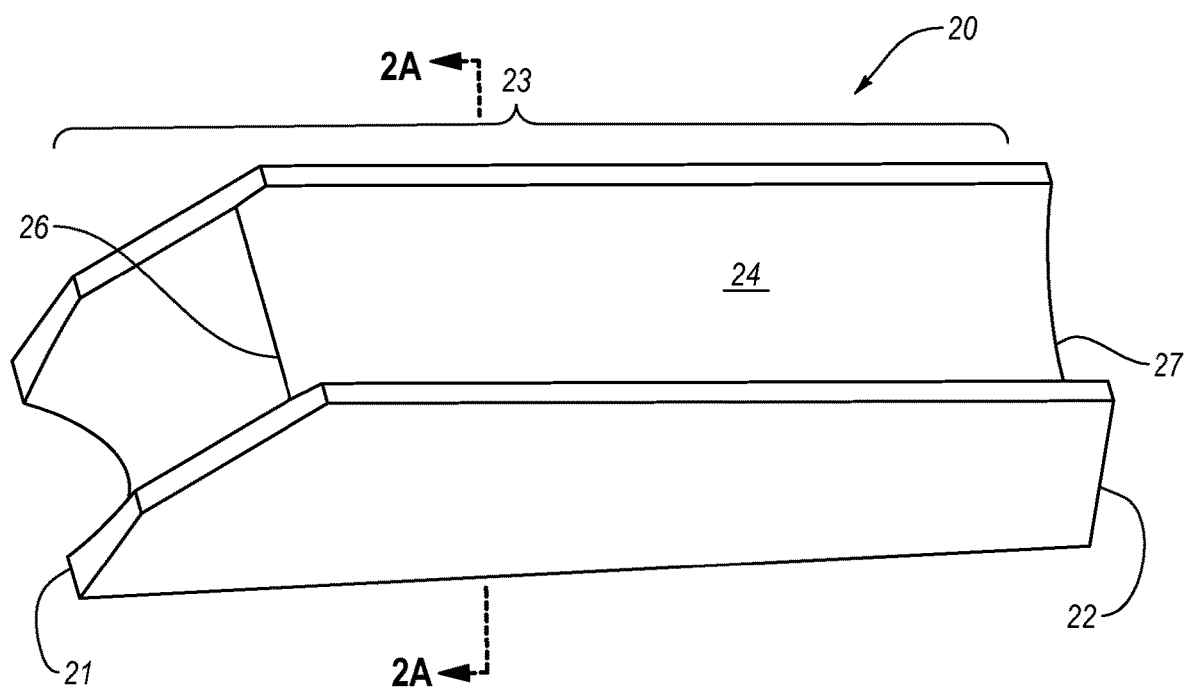
FIG. 2 is an alternative embodiment of an extremity-supporting base having a downward sloping concave trough and being open at a distal end.
Figure 2A:
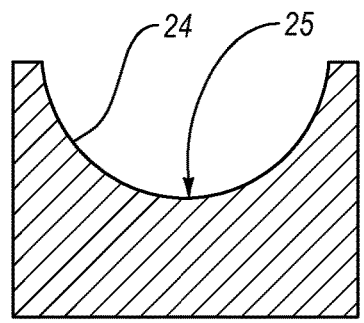
FIG. 2A is a transverse cross-sectional view of FIG. 2.

Referring now to FIG. 2, another embodiment of an extremity-supporting base 20 is illustrated. Some features of base 20 are the same as those of base 10 with two primary exceptions: extremity-supporting base 20 has neither a base dam nor a base drainage opening (such as elements 18 and 19, respectively, shown in FIG. 1). Otherwise, base 20 includes a proximal end 21, a distal end 22, a length 23, a trough 24, a trough bottom 25 (shown in FIG. 2A, which is a cross-sectional view of base 20 viewed from distal end 22), a trough bottom high point 26, and a trough bottom low point 27. Thus, trough 24 slopes downwardly toward distal end 22 (i.e., the extremity-supporting base 20 has a height that decreases from a point near the proximal end 21 to the distal end 22 so that the trough 24 slopes downwardly between the proximal end 21 and the distal end 22). Extremity-supporting base 20 is depicted as being open at the proximal end 21 and open at the distal end 22 to enable fluid to move distally along the trough 24 toward and beyond the distal end 22 of the trough 24. Base 20 also provides a continuous support surface of fixed length that is downwardly sloped at a constant angle of decline along an entirety of the trough 24. Trough 24 is illustrated as sloping downward from the high point 26 to the low point 27 at a constant angle of decline. As illustrated, trough 24 includes two opposing sidewalls what can be parallel to each other.

Like base 10, base 20 is designed for use as a support for a patient extremity, such as an arm or a leg, during the process of tissue debridement. Because base 20 does not have a base dam or a base drainage opening, an embodiment of a barrier shroud (discussed below) that cooperates with base 20 may be different than the shroud embodiment designed to cooperate with base 10. Specifically, the shroud drainage opening does not align with a base drainage opening when using base 20 because base 20 has no base drainage opening. In one embodiment, base 20 may be used with and support a barrier shroud having a shroud dam and a shroud drainage opening that are positioned beyond distal end 22 of base 20, as will be discussed in more detail below.

Like base 10, base 20 may be made of open-cell foam and may have a coating that is fluid-impermeable and flexible. The coating on base 20 may be formed of a polymeric, non-latex composition.

Although not depicted in the drawings, base 10 may operate together with a shroud that has a shroud drainage opening and a drainage hose that cooperate with base drainage opening 18 of base 10 such that the shroud includes a drainage opening which substantially lines up over base drainage opening 18 and a drainage hose that fits down and through base drainage opening 18 and extends beyond an underside of base 10.

Figure 3:
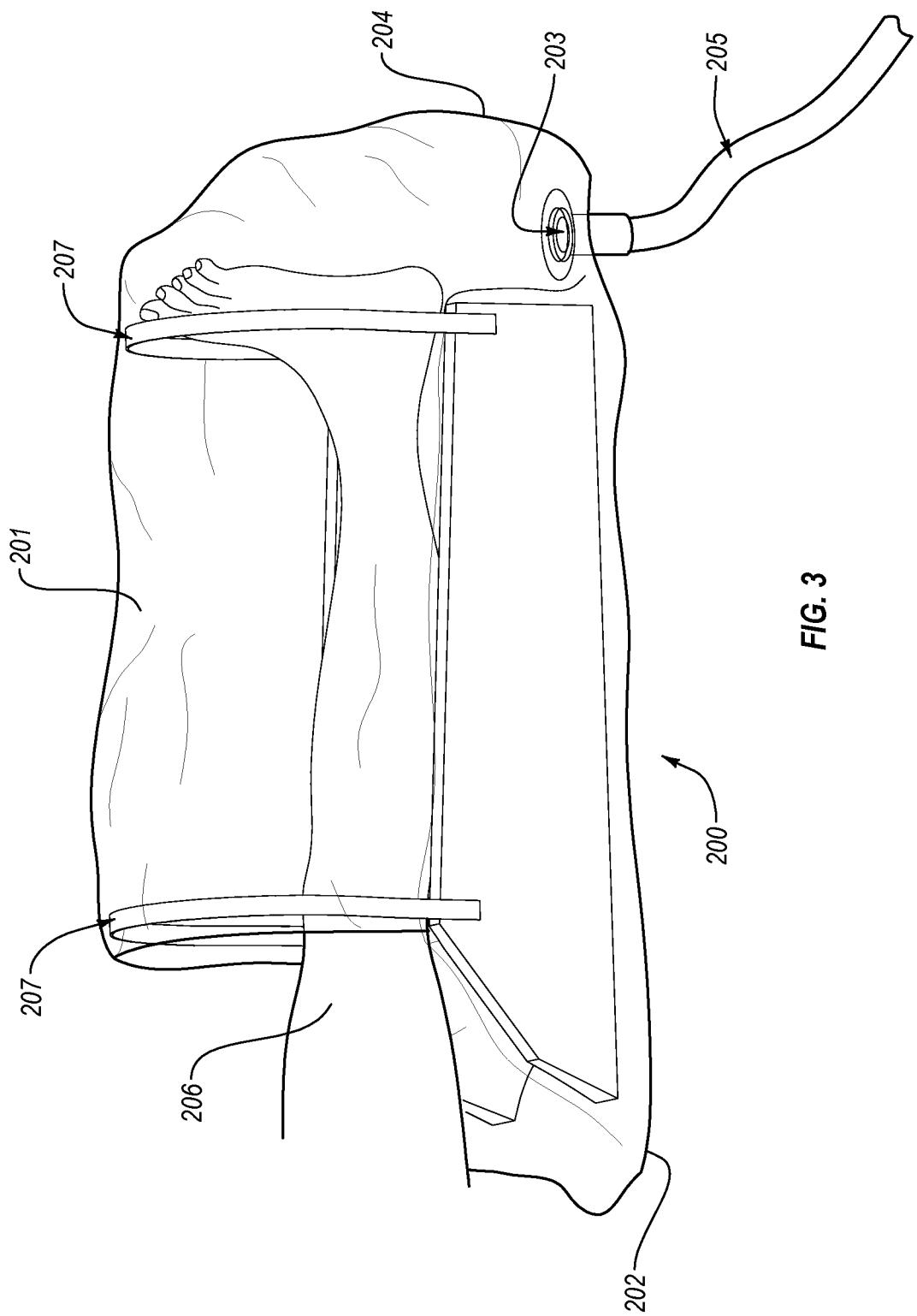
FIG. 3 illustrates an example embodiment of an apparatus for supporting an extremity during tissue debridement and capturing fluid and tissue, which includes a base supporting an extremity (i.e., leg) and a flexible barrier shroud partially enclosing the extremity.

FIG. 3 illustrates an extremity-supporting base similar to base 20 in cooperation with an embodiment of a barrier shroud 200. This embodiment of shroud 200 as shown has a top portion 201, a bottom portion 202, and a shroud drainage opening 203. A shroud dam 204 is formed by a raised or vertical portion just beyond shroud drainage opening 203 interconnecting top portion 201 and bottom portion 202. Shroud drainage opening 203 is attached to a drainage hose 205 that extends down and leads away from shroud 200. Shroud dam 204 is positioned beyond and below a distal end of the base in close proximity to shroud drainage opening 203 such that the excess fluid and tissue debris associated with tissue debridement may pool in an area of shroud 200 beyond and below the distal end of the base. Fluid and tissue may exit shroud drainage opening 203 with the aid of gravity and/or applied vacuum suction.

The availability of vacuum suction may alternatively permit shroud drainage opening 203 to be alternatively located in other regions of the shroud 200, such as in dam 24 or even top portion 201 of shroud 200 if top and bottom portions 201, 202 of shroud 200 are sealed at all points except the opening adjacent to the proximal end of the base.

One purpose of barrier shroud 200 is to contain fluid and removed tissue that may tend to spatter or be emitted from patient extremity 206 during the debridement process. Consistent with this purpose, the material for shroud 200 is advantageously fluid-impermeable or fluid-resistant. However, since shroud 200 is intended only for a single use and need not endure repeated exposure to fluid, materials that are not strictly fluid-resistant or fluid-impermeable may suffice.

In use, shroud 200 is positioned over patient extremity 206 such that bottom portion 202 of shroud 200 lies beneath extremity 206 but above the base, which supports the shroud-encased patient extremity 206. Top portion 201 of shroud 200 further includes one or a plurality of braces 207 operatively associated with top portion 201, although two braces 207 are shown in this illustrated embodiment. One purpose of brace 207 is to suspend top portion 201 over patient extremity 206 such that top portion 201 does not come into substantial contact with patient extremity 206. Another purpose of brace 207 is to provide the surgeon and medical staff with sufficient working space above patient extremity 206 but below top portion 201 so as to allow for the effective carrying out of a hydrosurgical debridement procedure.

The material used for brace 207 and the mechanism for operatively relating brace 207 with top portion 201 may be selected from any of a number of materials and methods consistent with accomplishing these purposes. Brace 207 may be operatively associated with top portion 201 in any of a number of conventional ways, including, but not limited to, being slidably positioned in a slot formed in top portion 201, fixedly attached to top portion 201 with adhesive, or integrally formed into the material of top portion 201 during manufacture. Brace 207 may be of fixed shape, such as the arcuate shape illustrated in FIG. 3, or may be of a deformable material, such as a soft metal, that can be manipulated into a desired shape.

Figure 4:
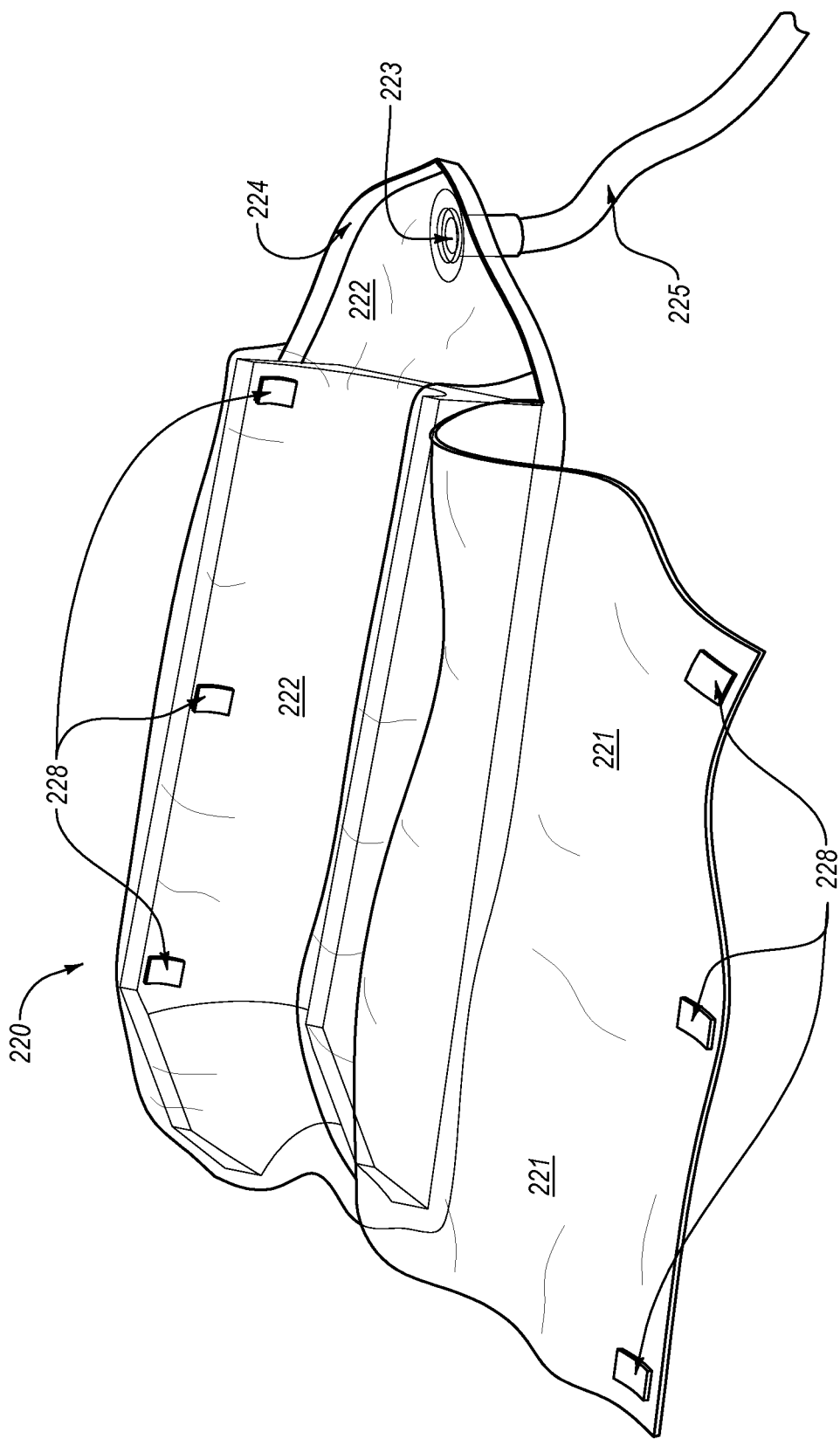
FIG. 4 illustrates another embodiment of an apparatus for supporting an extremity during tissue debridement and capturing fluid and tissue, which includes an extremity-supporting base and a flexible barrier shroud with fasteners that permit selective fastening and unfastening of the shroud during placement and removal of an extremity on the base.

Shroud 200 of FIG. 3 may be formed in a manner similar to that shown in FIG. 4 such that top portion 201 opens like a flap, or the top part of a sleeping bag, wherein top portion 201 is permanently joined to bottom portion 202 along one edge of shroud 200 (adjacent the length 23 of the base 20) and is attachable to bottom portion 202 along the opposite edge using known fastening devices such as snaps, Velcro® (hook and loop), buttons, clasps, hooks or zippers.

Top portion 201 and bottom portion 202 of shroud 200 may be joined in the manner shown in FIG. 3, that is, permanently joined along both opposing side edges and may or may not be permanently joined along the bottom edge, adjacent distal end of the base 20.

Figure 7:
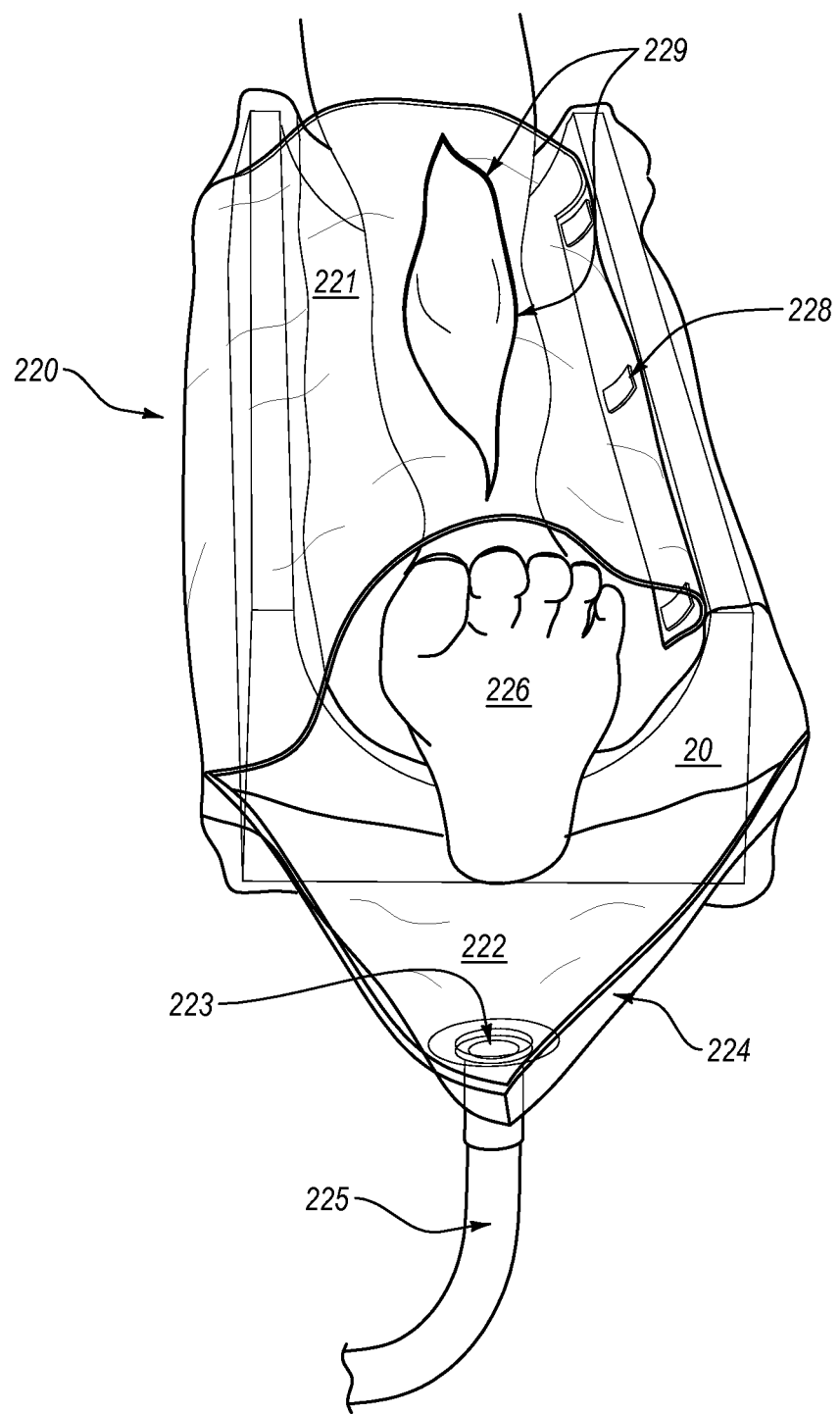
FIG. 7 illustrates an embodiment of an apparatus for supporting an extremity during tissue debridement and capturing fluid and tissue attached to a drainage tube in which the shroud includes an opening in an upper portion to facilitate access by a debridement instrument to the patient extremity.

Shroud 200 may also include one or more slit openings, such as the opening 229 shown in FIG. 7, formed in top portion 201 so as to allow access to patient extremity 206 by a debridement instrument during a debridement procedure.

Referring now to FIG. 4, another embodiment of an illustrative shroud 220 is shown. The features of shroud 220 are similar to those of shroud 200 shown in FIG. 3, with three primary exceptions: shroud 220 has no brace 207; shroud 220 is open at both ends, not just at the end associated with the proximal end of the base; and shroud 220 has a separate shroud wall or dam 224 formed into or attached to a bottom portion 222 and does not, as is illustrated in FIG. 3, rely upon the region where the top and bottom portions meet to function as the shroud dam. Otherwise, shroud 220 has a top portion 221, a bottom portion 222, a shroud drainage opening 223, a shroud wall or dam 224 distal of said drainage opening 223, and a drainage hose 225.

Shroud dam 224 can be a ridge-like structure formed into bottom portion 222 of shroud 220 and may be positioned beyond and below the distal end of the base in close proximity to shroud drainage opening 223 such that fluid and tissue debris associated with debridement may pool in the area near shroud drainage opening 223 and exit shroud drainage opening 223 with the aid of either gravity or applied vacuum suction. Alternatively, shroud dam 224 may be a separately formed structure that is fixedly attached to shroud bottom 222 using known methods, such as heat to the shroud dam 224 to shroud bottom portion 222, or glue, or other adhesives.

As can be seen in FIG. 4, top portion 221 can open and close like a flap, and shroud 220 is open at both ends adjacent the proximal and distal ends of the base. Top portion 221 is permanently joined to bottom portion 222 along one edge of shroud 220 and is releasably attachable to bottom portion 222 along the opposite edge using known fastening devices 228 such as snaps, Velcro®, buttons, hooks, clasps or zippers. As illustrated in FIGS. 4-7, shroud 220 can fully enclose the extremity-supporting base, including the entire bottom surface of the extremity supporting base.

Figure 5:
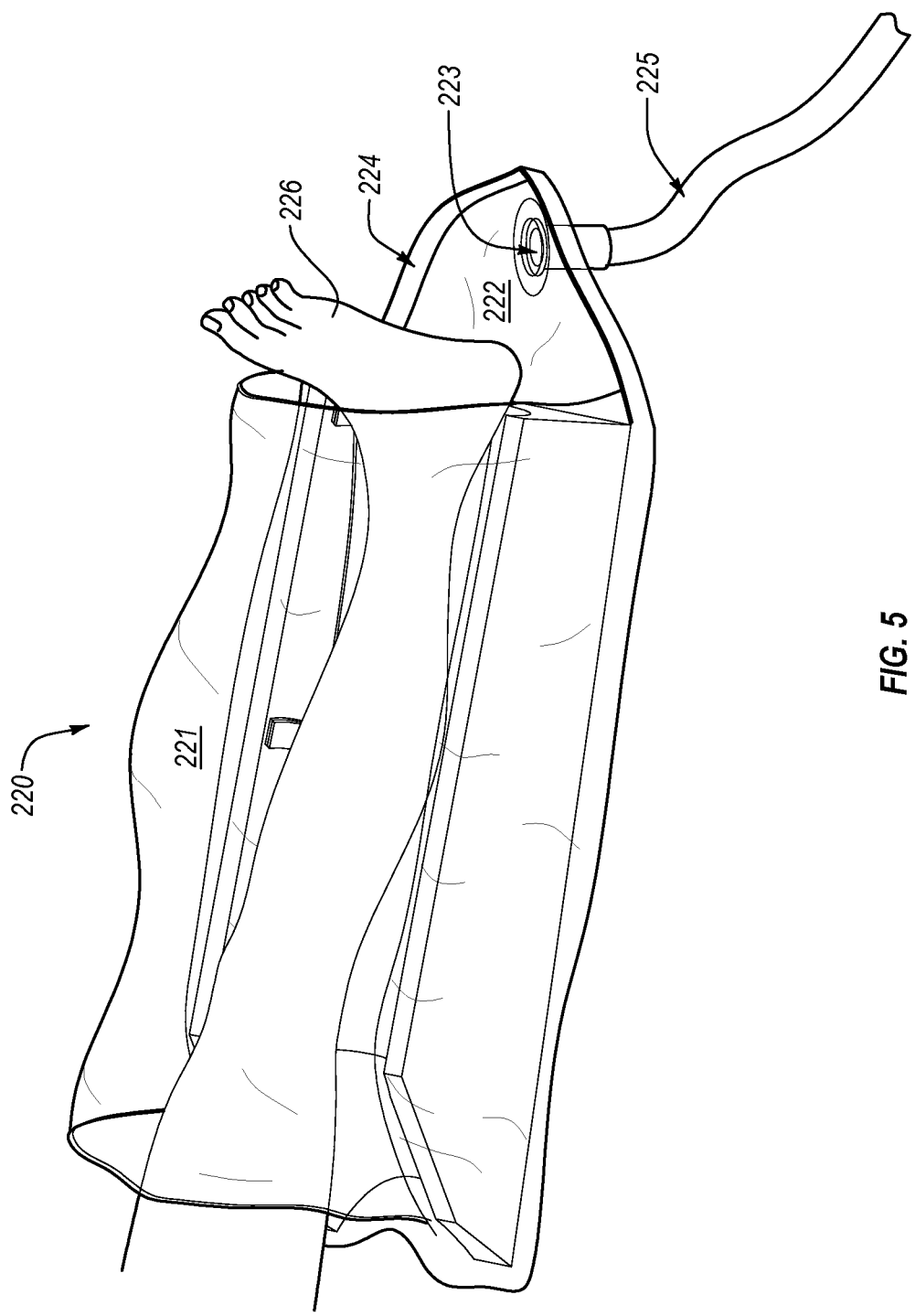
FIG. 5 illustrates an embodiment of an apparatus for supporting an extremity during tissue debridement and capturing fluid and tissue attached to a drainage tube and a patient extremity ready to undergo tissue debridement.
Figure 6:
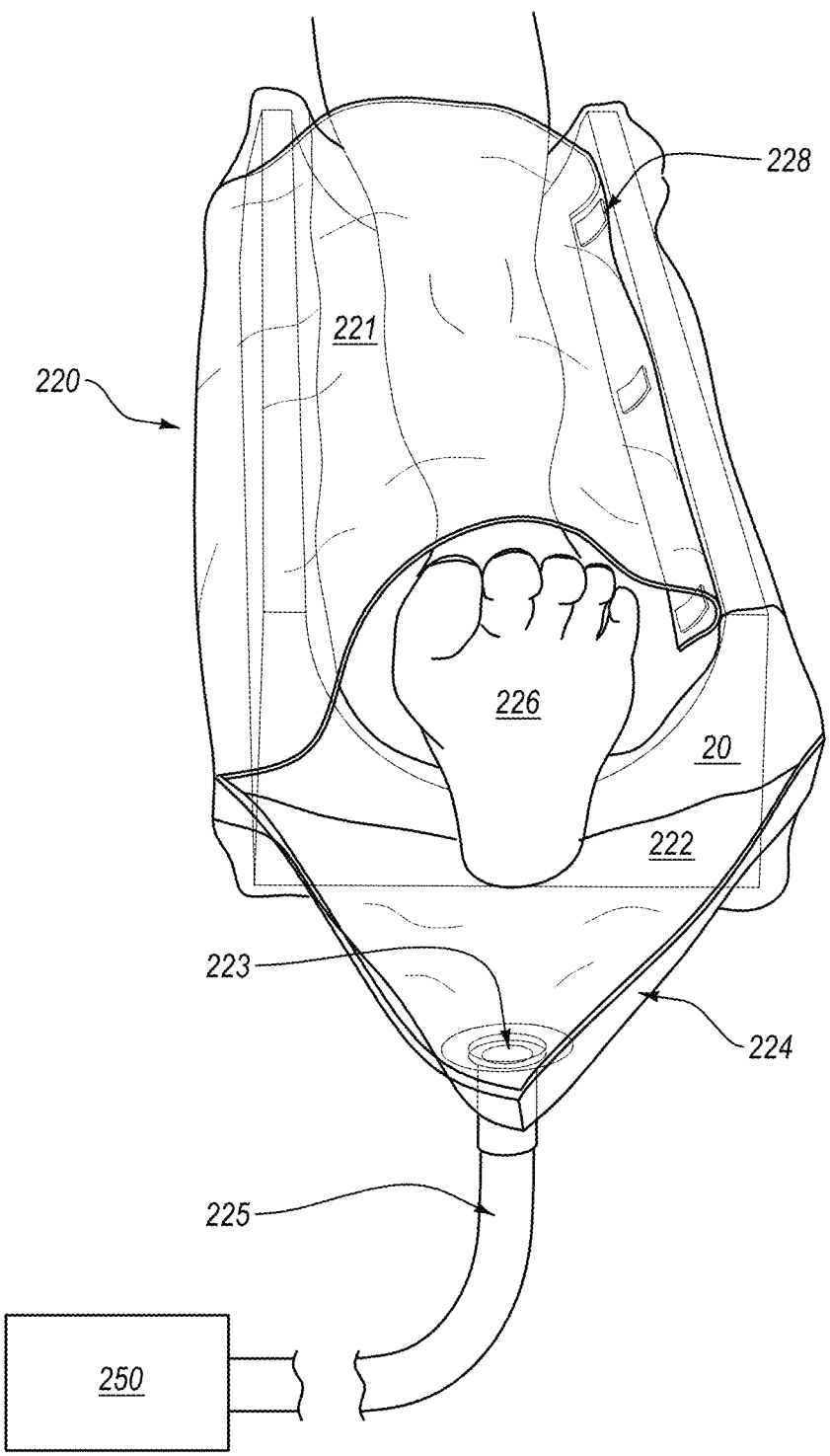
FIG. 6 is an alternative view of the embodiment illustrated in FIG. 5.

FIGS. 5-7 show the embodiment of FIG. 4 in use, where the base and shroud 220 cooperate to support and enclose a patient extremity 226. FIG. 5 illustrates an aspiration device 250 for applying suction to drainage hose 225. FIG. 6 shows the same configuration of base 20 and shroud 220, but viewed from the distal end 22 of the base 20 towards the proximal end 21 of the base 20. FIG. 7 is the same as FIG. 6 but illustrates the incorporation of at least one opening 229, in the form of a slit in the embodiment shown, in top portion 221 of shroud 220 so as to allow access to patient extremity 226 by the debridement instrument being operated by the medical personnel.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for supporting an extremity during tissue debridement and capturing fluid and tissue resulting from tissue irrigation and debridement, comprising:
    an extremity-supporting base configured to support an extremity of a patient during tissue irrigation and debridement, said extremity-supporting base having
    a proximal end positioned nearest a patient's body during use,
    a distal end opposite said proximal end,
    a bottom surface,
    a support surface, and
    a total of two opposing sidewalls extending above the support surface and longitudinally along sides of the support surface,
    the support surface and the two opposing sidewalls forming a trough of fixed length longitudinally extending from a point near the proximal end of the extremity-supporting base to the distal end of the extremity-supporting base and being adapted for placement and support of the extremity thereon,
    said extremity-supporting base having a height that decreases from said point near said proximal end to said distal end so that said trough slopes downwardly between said proximal end and said distal end,
    the extremity-supporting base being open at the proximal end and open at the distal end to enable fluid to move distally along the trough toward and beyond the distal end of the trough;
    a barrier shroud positionable and adapted so as to at least partially enclose an extremity supported by said support surface; and a drainage opening disposed in said barrier shroud that provides controlled drainage of fluid during tissue irrigation and debridement, the drainage opening being positioned to receive fluid passing distally beyond a distal end of the trough.

2. An apparatus as in claim 1, wherein said barrier shroud comprises a flexible sheet material.

3. An apparatus as in claim 2, further comprising one or more braces that cooperate with said flexible sheet material of said barrier shroud to maintain said barrier shroud in a desired elevated configuration above said extremity-supporting base and relative to an extremity during tissue irrigation and debridement.

4. An apparatus as in claim 2, further comprising one or more fasteners attached to a free end of said barrier shroud and that permit selective opening and closing of said barrier shroud.

5. An apparatus as in claim 2, said barrier shroud including a bottom portion positioned on said support surface and adapted to lie between an extremity and said support surface during tissue irrigation and debridement.

6. An apparatus as in claim 1, further comprising a drainage tube in fluid communication with said drainage opening of said shroud for drainage of fluid and tissue into a receiving vessel.

7. An apparatus as in claim 6, further comprising an aspiration device for aspirating fluid and tissue through said drainage tube.

8. An apparatus as in claim 1, wherein said extremity-supporting base comprises an open-cell foam material.

9. An apparatus as in claim 8, wherein said extremity-supporting base further comprises a flexible, fluid-impermeable coating over said open-cell foam material.

10. An apparatus as in claim 1, wherein said downwardly sloped trough provides a continuous support surface of fixed length that is downwardly angled at a constant angle of decline along an entirety of said trough to facilitate movement of fluid and tissue toward said drainage opening of said shroud during tissue irrigation and debridement.

11. An apparatus as in claim 1, wherein said barrier shroud further includes a wall or dam distal of said drainage opening that assists in directing fluid and tissue toward said drainage opening during tissue irrigation and debridement.

12. An apparatus as in claim 1, wherein the two opposing sidewalls are parallel to each other.

13. An apparatus as in claim 1, wherein the barrier shroud is adapted to fully enclose the extremity-supporting base, including the bottom surface of the extremity-supporting base.

14. An apparatus for supporting an extremity during tissue debridement and capturing fluid and tissue resulting from tissue irrigation and debridement, comprising:

an extremity-supporting base formed from a polymer foam material configured to support an extremity of a patient during tissue irrigation and debridement, said polymer foam material of said extremity-supporting base having
a proximal end positioned nearest a patient's body during use and
a distal end opposite said proximal end,
said polymer foam material of said extremity-supporting base forming a trough of fixed length extending from a point near said proximal end to said distal end and configured to provide a support surface for an extremity,
wherein the trough includes a high point disposed near the proximal end of the extremity-supporting base and a low point at the distal end of the extremity-supporting base, the trough sloping downward from the high point to the low point at a constant angle of decline;
a barrier shroud that is positionable and adapted to at least partially enclose an extremity placed in said trough of said extremity-supporting base; and
a drainage passageway at or near said distal end of said extremity-supporting base in fluid communication with said barrier shroud.

15. An apparatus as in claim 14, wherein said drainage passageway comprises a single drainage hole through said barrier shroud through which both fluid and tissue can drain during a tissue irrigation and debridement procedure.

16. An apparatus as in claim 15, wherein the distal end of the extremity-supporting base is open to enable fluid to move distally along the trough toward and beyond the distal end of the extremity-supporting base.

17. An apparatus as in claim 15, wherein said drainage passageway is disposed distal of a distal end of the trough to enable collection of fluid passing distally beyond the trough.

18. An apparatus as in claim 14, wherein the barrier shroud is adapted to fully enclose the extremity-supporting base, including the bottom surface of the extremity-supporting base.

19. An apparatus for supporting an extremity during tissue debridement and capturing fluid and tissue resulting from tissue debridement, comprising:

an extremity-supporting base formed from a polymer foam material and configured and adapted to support an extremity of a patient during tissue debridement, said extremity-supporting base having
a proximal end positioned nearest a patient's body during use,
a distal end opposite said proximal end,
a bottom surface, and
a support surface of fixed length,
wherein said extremity-supporting base has a height that decreases from a point near said proximal end to said distal end so that said support surface is downwardly sloped between said proximal end and said distal end;
a barrier shroud positionable and adapted to fully enclose the extremity-supporting base, including the entire bottom surface of the extremity-supporting base, and adapted to at least partially enclose an extremity supported by said support surface of said extremity-supporting base; and
a drainage passageway in fluid communication with said barrier shroud that provides controlled drainage of fluid and tissue during tissue irrigation and debridement.

20. An apparatus as in claim 19, wherein said drainage passageway contains a single drainage hole through which both fluid and tissue can drain during a tissue irrigation and debridement procedure.

* * * * *